(12) United States Patent
Roehrlein et al.

(10) Patent No.: US 9,968,781 B2
(45) Date of Patent: May 15, 2018

(54) IMPLANTABLE HEARING ASSISTANCE APPARATUS AND CORRESPONDING SYSTEMS AND METHODS

(71) Applicant: Advanced Bionics AG, Staefa (CH)

(72) Inventors: Gerhard Roehrlein, Staefa (CH); Stefan Launer, Zurich (CH); Lee F. Hartley, Valencia, CA (US); Lakshmi Mishra, Carlsbad, CA (US); Abhijit Kulkarni, Newbury Park, CA (US); Logan P. Palmer, Santa Monica, CA (US); Mark Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 10 days.

(21) Appl. No.: 15/125,151

(22) PCT Filed: Mar. 22, 2014

(86) PCT No.: PCT/US2014/031527
§ 371 (c)(1),
(2) Date: Sep. 10, 2016

(87) PCT Pub. No.: WO2015/147772
PCT Pub. Date: Oct. 1, 2015

(65) Prior Publication Data
US 2016/0375242 A1    Dec. 29, 2016

(51) Int. Cl.
*A61N 1/00* (2006.01)
*A61N 1/36* (2006.01)
*H04R 25/00* (2006.01)
*A61N 1/372* (2006.01)
*A61N 1/05* (2006.01)
*A61N 1/378* (2006.01)

(52) U.S. Cl.
CPC ..... *A61N 1/36032* (2013.01); *A61N 1/36038* (2017.08); *A61N 1/37223* (2013.01); *H04R 25/554* (2013.01); *A61N 1/0541* (2013.01); *A61N 1/3787* (2013.01); *H04R 2225/021* (2013.01)

(58) Field of Classification Search
CPC ............. A61N 1/0541; A61N 1/36032; A61N 1/36038; A61N 1/37223; A61N 1/3787; H04R 2225/021; H04R 25/554
See application file for complete search history.

(56) References Cited

U.S. PATENT DOCUMENTS

| | | |
|---|---|---|
| 4,918,745 A | 4/1990 | Hitchison |
| 5,751,820 A | 5/1998 | Taenzer et al. |

(Continued)

FOREIGN PATENT DOCUMENTS

| | | |
|---|---|---|
| WO | WO2013008057 | 1/2013 |
| WO | WO2014003777 | 1/2014 |
| WO | WO2014035379 | 3/2014 |

OTHER PUBLICATIONS

PCT International Search and Written Opinion dated Jul. 14, 2014 for PCT App. Ser. No. PCT/US2014/031527.

*Primary Examiner* — George Manuel
(74) *Attorney, Agent, or Firm* — Henricks, Slavin & Holmes LLP

(57) ABSTRACT

Hearing assistance apparatus, systems and methods that involve the use of a head mountable power supply to power an implantable cochlear stimulator.

27 Claims, 6 Drawing Sheets

(56) References Cited

U.S. PATENT DOCUMENTS

| | | |
|---|---|---|
| 5,824,022 A | 10/1998 | Zilberman et al. |
| 6,775,389 B2 | 8/2004 | Harrison et al. |
| 6,842,647 B1 | 1/2005 | Griffith |
| 7,003,353 B1 | 2/2006 | Parkhouse |
| 7,039,466 B1 | 5/2006 | Harrison et al. |
| 7,450,994 B1 * | 11/2008 | Mishra .................. A61B 5/442 607/57 |
| 7,599,508 B1 | 10/2009 | Lynch et al. |
| 8,027,733 B1 | 9/2011 | Fridman et al. |
| 8,073,171 B2 | 12/2011 | Haenggi et al. |
| 8,270,647 B2 | 9/2012 | Crawford et al. |
| 8,515,112 B2 | 8/2013 | Crawford et al. |
| 8,811,643 B2 | 8/2014 | Crawford et al. |
| 8,983,102 B2 | 3/2015 | Crawford et al. |
| 9,392,384 B2 | 7/2016 | Crawford et al. |
| 2003/0171787 A1 | 9/2003 | Money et al. |
| 2004/0172102 A1 * | 9/2004 | Leysieffer .......... A61N 1/36036 607/57 |
| 2005/0159791 A1 | 7/2005 | Daly et al. |
| 2005/0209657 A1 | 9/2005 | Chung et al. |
| 2006/0190059 A1 | 8/2006 | Griffith |
| 2007/0027676 A1 | 2/2007 | Chambers et al. |
| 2007/0282394 A1 | 12/2007 | Segel et al. |
| 2008/0002834 A1 | 1/2008 | Hochmair |
| 2008/0177353 A1 | 7/2008 | Hirota et al. |
| 2008/0300658 A1 * | 12/2008 | Meskens .................. A61N 1/08 607/60 |
| 2009/0216296 A1 | 8/2009 | Meskens |
| 2009/0292338 A1 | 11/2009 | Gordon et al. |
| 2010/0046778 A1 | 2/2010 | Crawford et al. |
| 2010/0198303 A1 | 8/2010 | Haller et al. |
| 2012/0041515 A1 | 2/2012 | Meskens et al. |
| 2012/0109297 A1 | 5/2012 | Van den Heuvel |
| 2012/0150259 A1 | 6/2012 | Meskens |
| 2012/0316618 A1 | 12/2012 | Zierhofer et al. |
| 2013/0066398 A1 | 3/2013 | Duftner et al. |
| 2014/0025138 A1 | 1/2014 | Meskens et al. |
| 2014/0064528 A1 | 3/2014 | Flood et al. |
| 2016/0375243 A1 | 12/2016 | Roehrlein et al. |
| 2017/0028199 A1 | 2/2017 | Roehrlein et al. |

* cited by examiner

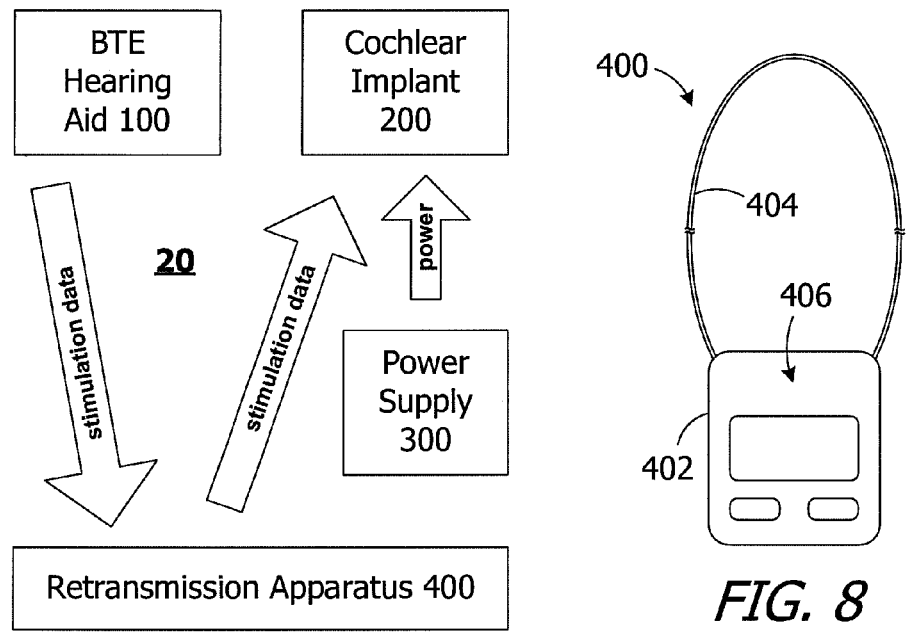
*FIG. 7*
*FIG. 8*
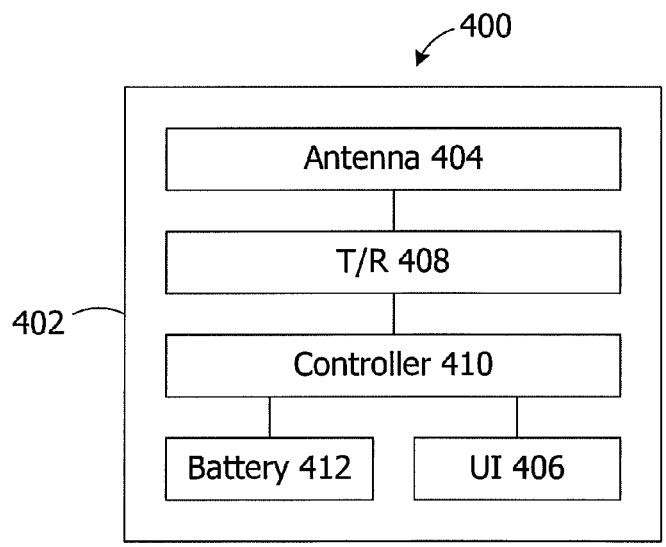
*FIG. 9*

IMPLANTABLE HEARING ASSISTANCE APPARATUS AND CORRESPONDING SYSTEMS AND METHODS

CROSS-REFERENCE TO RELATED APPLICATIONS

This application is the U.S. National Stage of PCT App. Ser. No. PCT/US2014/031527, filed Mar. 22, 2014.

BACKGROUND

1. Field

The present disclosure relates generally to hearing assistance devices such as, for example, implantable cochlear stimulation ("ICS") systems and hearing aids.

2. Description of the Related Art

A wide variety of hearing assistance devices are available. Such devices include, but are not limited to, ICS systems and hearing aids.

ICS systems are used to help the profoundly deaf perceive a sensation of sound by directly exciting the auditory nerve with controlled impulses of electrical current. Ambient sound pressure waves are picked up by an externally worn microphone and converted to electrical signals. The electrical signals, in turn, are processed by sound processor circuitry, converted to stimulation data (e.g., a pulse sequence having varying pulse widths and/or amplitudes), and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. Alternatively, the implantable electrode array may be directly inserted into the cochlear nerve without residing in the cochlea.

ICS systems commonly include an implantable device, an external sound processor, with the sound processor circuitry, and a microphone that is in communication with the sound processor circuitry. In one type of ICS system, the sound processor is worn behind the ear (a "BTE sound processor"). The sound processor transmits stimulation data, as well as power from its battery, to the implantable device by way of an inductive link. To that end, ICS systems include a headpiece that is connected to the sound processor by a cable. The headpiece has a coil antenna that is used to connect to the headpiece (and BTE sound processor by way of the headpiece) to the implantable device via an inductive link. So configured, the BTE sound processor provides sound processing functionality and also provides power for the entire ICS system. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor. Other ICS systems are configured such that all of the components (e.g., the battery, the microphone, the sound processor, and the coil) are carried within a single headpiece. One example of such a system is disclosed in U.S. Pat. Pub. No. 2010/0046778, which is entitled "Integrated Cochlear Implant Headpiece" and incorporated herein by reference in its entirety.

Hearing aids include a microphone, sound processor circuitry, and a speaker (sometimes referred to as a "receiver"). Here too, ambient sound pressure waves are picked up by the microphone and converted into electrical signals. The electrical signals, in turn, are processed by sound processor circuitry. The processed signals drive the speaker, which delivers amplified (or otherwise processed) sound pressure waves to the ear canal. Exemplary types of hearing aids include, but are not limited to, BTE hearing aids, receiver-in-canal ("RIC") hearing aids, in-the-canal ("ITC") hearing aids and completely-in-the-canal ("CIC") hearing aids. Examples of commercially available hearing aids include, but are not limited to, the Phonak™ Ambra™ hearing aid and the Phonak™ Naida™ hearing aid.

The present inventors have determined that conventional ICS systems are susceptible to improvement. For example, the present inventors have determined that economies of scale and various regulatory issues make hearing aids a more desirable platform for ICS system sound processing than conventional cochlear implant BTE sound processor and body worn sound processors. The present inventors have also determined that some patients find the wire that extends from the sound processor to the headpiece to be undesirable and that some patients would benefit from a sound processor that can be used in an ICS system, but is smaller than those currently available.

SUMMARY

A head mountable power supply in accordance with one of the present inventions includes a housing, a battery, a magnet that is magnetically attracted to the position element of an implanted cochlear stimulator, and a power transmission apparatus carried by the housing, operably connected to the battery and configured to wirelessly supply power to the implanted cochlear stimulator. The head mountable power supply does not include a data communication apparatus that transmits data.

A hearing assistance system in accordance with one of the present inventions includes an implantable cochlear stimulator, an external hearing assistance device including a battery, sound processor circuitry that converts electrical signals from a microphone into stimulation data, and a data communication apparatus configured to wirelessly transmit the stimulation data used by the implantable cochlear stimulator, and a head mountable power supply including a battery, a magnet that is magnetically attracted to the position element, and a power transmission apparatus operably connected to the battery and configured to wirelessly supply power to the implantable cochlear stimulator.

A method in accordance with one of the present inventions includes the steps of wirelessly transmitting stimulation data from an external hearing assistance device associated with a user's head to a cochlear stimulator implanted within the user's head, wirelessly transmitting power stored in a battery of an external power supply, which is not connected to hearing assistance device and is mounted on the exterior of the user's head by way of magnetic attraction between the power supply and the implanted cochlear stimulator, to the implanted cochlear stimulator, and electrically stimulating the user's auditory nerve with the implanted cochlear stimulator in response to receipt of the stimulation data from the external sound processor.

A hearing assistance system in accordance with one of the present inventions includes an implantable cochlear stimulator, a hearing assistance device with a microphone and data communication apparatus that wirelessly transmits electrical signals from the microphone, a retransmission apparatus, including a data communication apparatus and sound processor circuitry, that wirelessly receives electrical signals from the hearing assistance device, converts the electrical signals from a microphone into stimulation data, and wirelessly transmits the stimulation data to the implantable cochlear stimulator, a head mountable power supply that wirelessly supplies power to the implantable cochlear stimulator power receiver apparatus.

A hearing assistance system in accordance with one of the present inventions includes an implantable cochlear stimulator, a notification source that transmits a notification signal, a retransmission apparatus, including a data communication apparatus, that wirelessly receives the notification signal and wirelessly transmits stimulation data to the implantable cochlear stimulator in response to receipt of the notification signal, and a head mountable power supply configured to wirelessly supply power to the implantable cochlear stimulator power receiver apparatus.

There are a number of advantages associated with such apparatus, systems and methods. For example, the present hearing assistance device may be in the form of an otherwise conventional hearing aid that is modified so as to be capable of wirelessly communicating with an implanted cochlear stimulator. The use of a modified hearing aid is advantageous because, as compared to cochlear implant sound processors, hearing aids are manufactured in far greater quantities, are more frequently updated, and have fewer regulatory hurdles to overcome. Additionally, supplying power to an implanted cochlear stimulator with a battery carried by the headpiece eliminates the need for a headpiece cable and also facilitates a reduction in the size/weight of the external hearing assistance device that was heretofore attributable to the supply of power to the cochlear stimulator. The present apparatus, systems and methods may also be implemented in electric acoustic stimulation ("EAS") systems where a hearing aid and a cochlear implant are used together in the same ear.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 7 is a block diagram showing components of an ICS system in accordance with one embodiment of a present invention.

FIG. 8 is a plan view of a retransmission apparatus in accordance with one embodiment of a present invention.

FIG. 9 is block diagram of a retransmission apparatus in accordance with one embodiment of a present invention.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of hearing assistance devices and systems that provide sound (i.e., either sound or a perception of sound) to the hearing impaired as well as others who require such hearing devices on a situational basis. Examples of such hearing assistance devices and systems include hearing aids and ICS systems where an external sound processor communicates with a cochlear implant. The present inventions are not, however, limited to hearing aids and external ICS sound processors, and may be employed in combination with other hearing assistance devices that currently exist, or are yet to be developed.

Figure 1:
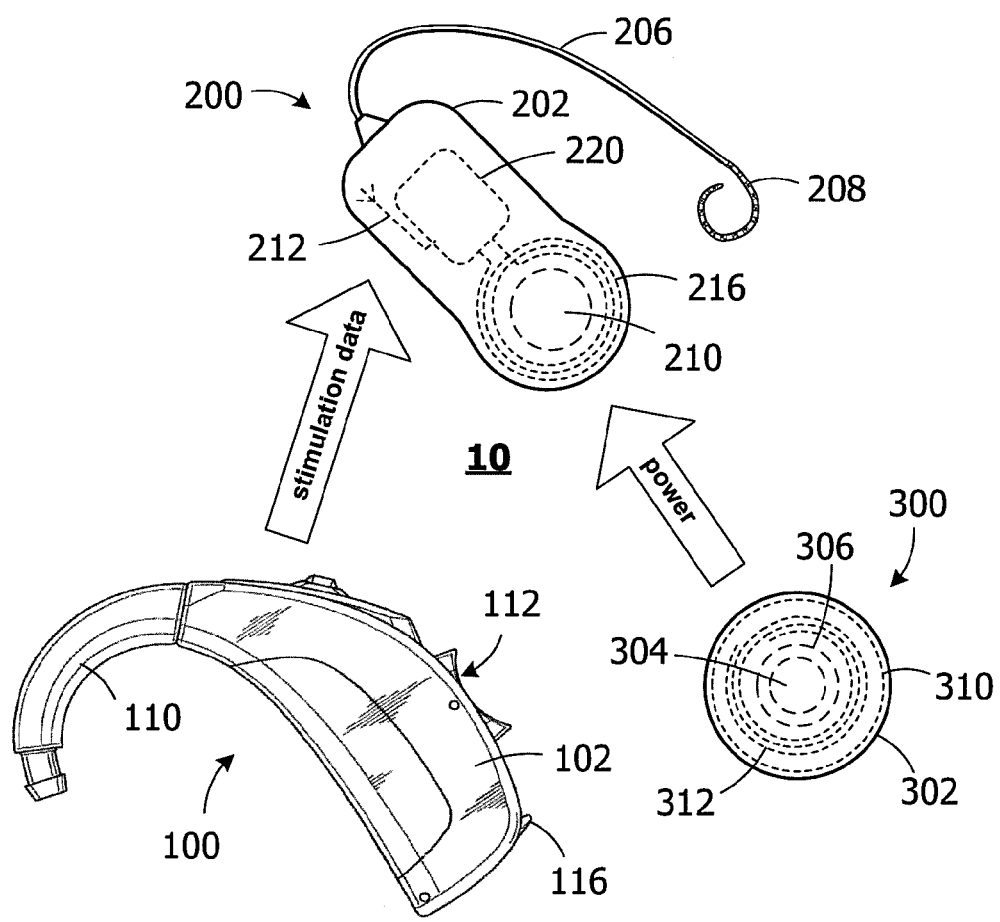
FIG. 1 is a plan view showing components of an ICS system in accordance with one embodiment of an present invention.

One example of a hearing assistance system is the ICS system generally represented by reference numeral 10 in FIG. 1. The exemplary ICS system 10 includes a BTE hearing aid 100 (or other external hearing assistance device), an implantable cochlear simulator 200, and an external head mountable power supply 300. Briefly, the BTE hearing aid 100 supplies stimulation data to the cochlear simulator 200 by way of a wireless data link, while the power supply 300 supplies power to the cochlear simulator by way of a wireless power link.

Figure 2:
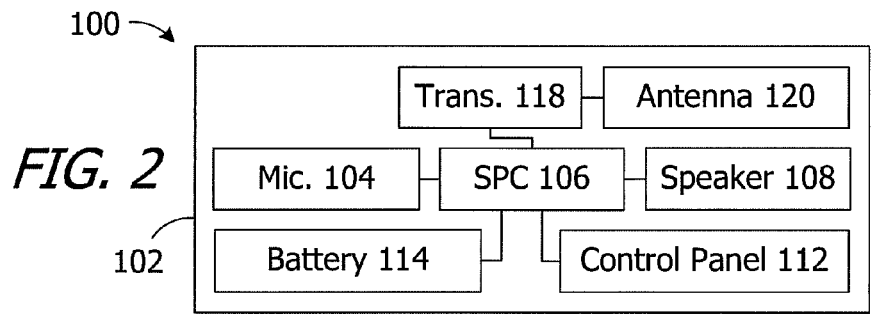
FIG. 2 is a block diagram of a hearing aid in accordance with one embodiment of a present invention.

Referring also to FIG. 2, the exemplary BTE hearing aid 100 includes a housing 102, a microphone 104, sound processor circuitry ("SPC") 106, and a speaker 108. A sound tube 110 may be associated with the speaker 108. A control panel 112 with components such as an ON/OFF switch and a volume control element is positioned on the exterior of the housing 102. The BTE hearing aid 100 also includes a primary or secondary battery or other power supply 114 that supplies power to the sound processor circuitry 106 and other power consuming components of the BTE hearing aid. In the illustrated implementation, the battery 114 is carried by a removable battery holder (not shown) that is secured to housing 102 with a latch 116. In other implementations, a secondary battery may be permanently housed within the hearing aid and the battery holder may be omitted. Such a hearing aid may be placed in a battery charger as necessary.

There is also a wireless data link between the BTE hearing aid 100 and the cochlear simulator 200. In the illustrated embodiment, a data transmitter 118 drives a data antenna 120 to transmit stimulation data, but not power, to the implantable cochlear simulator 200. The BTE hearing aid 100 does not supply power to the cochlear simulator 200.

The data transmitter 118 and data antenna 120 are collectively referred to as a data communication apparatus and, in those implementations where the BTE hearing aid wirelessly receives information (e.g., where status information is transmitted from the cochlear simulator 200 to the BTE hearing aid 100), the data communication apparatus would include a data transceiver and a data antenna. One example of a suitable data communication apparatus is a near field magnetic induction ("NFMI") apparatus where a data transmitter and coil antenna generate a short range, low-power, non-propagating magnetic field. Other types of wireless links, including but not limited to RF data communication apparatus, may also be employed.

Figure 3:
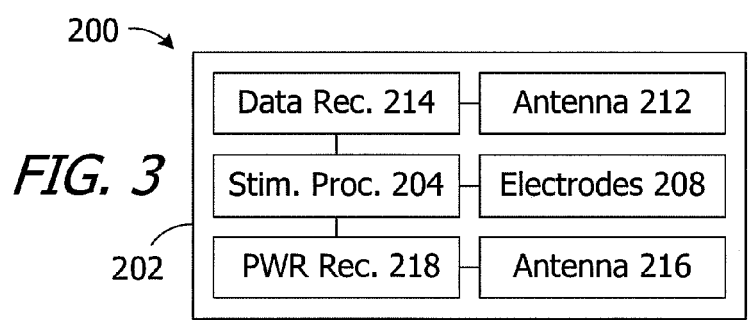
FIG. 3 is a block diagram of an implantable cochlear stimulator in accordance with one embodiment of a present invention.

As illustrated in FIGS. 1 and 3, the exemplary cochlear stimulator 200 includes a flexible housing 202 formed from a silicone elastomer or other suitable material, an internal stimulation processor 204, a cochlear lead 206 with an electrode array 208, and a positioning element (i.e., a magnet or other ferromagnetic material) 210. The cochlear stimulator 200 also includes data receiver apparatus and power receiver apparatus. In the illustrated implementation, data is received by way of a data antenna 212 and a data receiver 214 and power is received by way of a power antenna 216 and power receiver 218. The stimulation processor 204 and data and power receivers 214 and 218 may be located on a common circuit board 220, or on separate boards. The data antenna and receiver 212 and 214 are used to receive stimulation data from the BTE hearing aid 100, while a power antenna and receiver 216 and 218 receive power from the external power supply 300. The exemplary data receiver apparatus is an NFMI apparatus including a coil antenna. RF antennas and may also be employed as data receivers in other types of wireless links. The power antenna 216 may be a coil antenna that is inductively coupled to the power transmission coil antenna 314 (discussed below) of the external power supply 300.

As used herein, a "stimulation processor" is a processor that converts the stimulation data from a sound processing device (e.g., the sound processor circuitry 106) into stimulation signals that stimulate the electrodes of an electrode array (e.g., the electrodes in array 208). A "stimulation processor" does not itself convert electrical signals from a microphone into stimulation data and, therefore, is not a "sound processor." It should also be noted that the exemplary implantable cochlear stimulator 200 is not a totally implantable cochlear implant system, nor is it part of such a system. To that end, the cochlear stimulator 200 does not include a microphone, sound processor circuitry, or a battery. The cochlear stimulator 200 relies on other devices (here, the BTE hearing aid 100) for microphone and sound processing functionality and relies on another device (here, the external power supply 300) for power.

Figure 4:
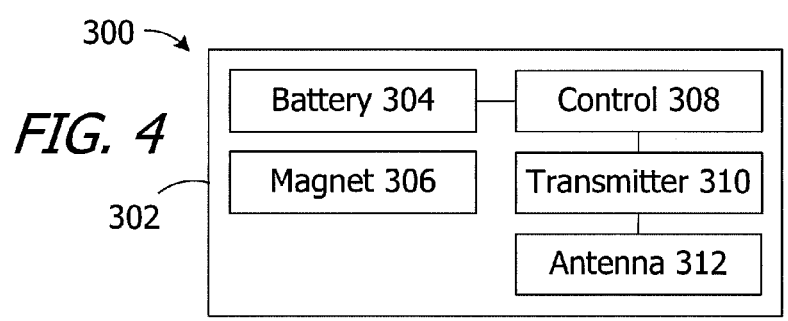
FIG. 4 is a block diagram of a head mountable power supply in accordance with one embodiment of a present invention.

As illustrated in FIGS. 1 and 4, the exemplary external head mountable power supply (or "headpiece power supply") 300 includes a housing 302, a battery 304 (primary or secondary), a positioning magnet 306 that is attracted to the positioning element 210 of the cochlear stimulator 200, power control circuitry 308 on a circuit board 310, a power transmission apparatus including a transmitter 312 that drives a coil antenna 314 (or other suitable antenna). The power control circuitry 310 controls the flow of power from the battery 304 to the transmitter 312 and coil antenna 314. In the illustrated embodiment, the transmitter 312 and antenna 314 generate a carrier with no data and form a close coupled inductive link with the power receiver antenna 216 of the cochlear stimulator 200. The housing 302 includes a battery replacement door (not shown) so that the battery 304 may be removed and replaced as necessary. Alternatively, the secondary battery may be permanently housed within the housing and the door may be omitted. Such a head mountable power supply may be placed in a battery charger as necessary. In the illustrated implementation, there is no on/off switch and the power supply 300 operates so long as the battery 304 is not fully discharged. An on/off switch may be provided in other implementations. A low power indicator such as an LED may be provided in some implementations. With respect to power transmission level, which is typically a function of the thickness of the skin between the power supply 300 and the cochlear stimulator 200, the power level may be preset as it is in the illustrated implementation. In others, a small knob may be provided that allows the power level to be adjusted during the fitting process.

The power supply 300 is used solely to supply power to the cochlear stimulator 200 and does not transmit cochlear stimulation data. To that end, the power supply 300 does not include a microphone or sound processor circuitry. The power supply 300 also does not communicate with the hearing aid 100 and there is no cable connecting the power supply to the hearing aid. It should also be noted that the present power head mountable power supply is commensurate in size and shape with a conventional ICS headpiece (e.g., is between about 0.25 inch and 3 inches in diameter in some implementations and between about 0.5 inch and 1.5 inch in other implementations) and is not a BTE device or part of a BTE device.

In at least some implementations, the cochlear stimulator 200 may provide the power supply 300 with information that can be used to, for example, optimize power transmission to the cochlear stimulator by adjusting the transmission level to a level below the maximum level, when possible, to extend the life of the battery 304. For example, information concerning the current supply voltage of the cochlear stimulator 200 may be used by the power supply 300 to modulate power to the cochlear stimulator in real time. The information may be provided in a variety of ways. For example, a low data rate back telemetry link from the cochlear stimulator 200, which is indicative of the tank voltage of the implant (e.g., a single bit which indicates whether the tank voltage is at or below a predetermined level), may be used by the power control circuitry 308 to modulate power from the power supply 300. Alternatively, the cochlear stimulator 200 may be configured to alter its effective impedance as a function of the tank voltage. The effective impendence can be detected by the power control circuitry 308 and used to modulate power from the power supply 300.

Figure 5:
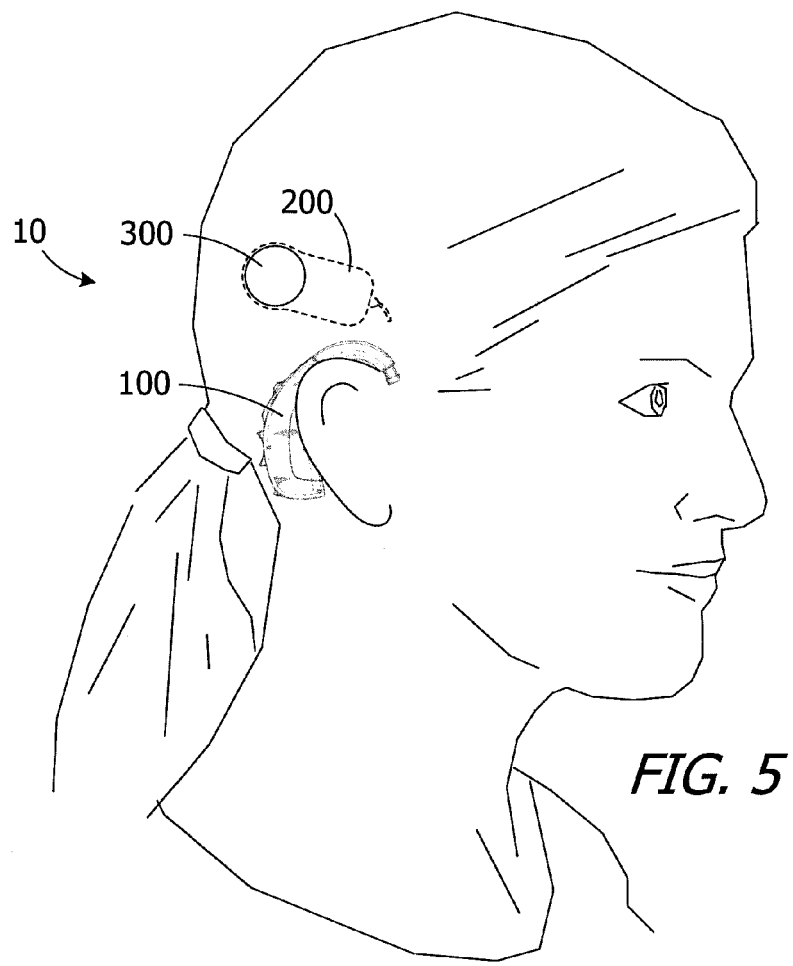
FIG. 5 is a side view showing the ICS system as illustrated in FIGS. 1-4 in use.

During use of the exemplary system 10, and as illustrated in FIG. 5, the BTE hearing aid 100 is positioned behind the ear and the power supply 300 is positioned over the implanted cochlear stimulator 200. The power supply 300 is not connected to the BTE hearing aid 100 by a cable. Nor is there wireless communication between BTE hearing aid 100 and the power supply 300. The attraction of the power supply magnet 306 to the stimulator magnet or other positioning element 210 aligns the power supply antenna 314 with the cochlear stimulator power receiver antenna 216. Power from the power supply 300 is supplied to the implanted cochlear stimulator 200. The hearing aid microphone 104 picks up ambient sound pressure waves and converts them into electrical signals. The electrical signals are the processed by the sound processor circuitry 106 and converted to stimulation data (e.g., a pulse sequence having varying pulse widths and/or amplitudes). The hearing aid data transmitter 118 and antenna 120 establish a wireless link with the cochlear stimulator data antenna and receiver 212 and 214 and transmit the stimulation data, but not power, to the implantable cochlear simulator 200. The antenna and receiver 212 and 214 receive the stimulation data and send the data to the stimulation processor 204 which, in turn, converts the data into stimulation signals that stimulate the electrodes in the array 208. The electrode array 208 electrically stimulates the auditory nerve inside the cochlea, thereby providing the user with sensory input that is a representation of external sound waves which were sensed by the microphone 104.

Figure 6:
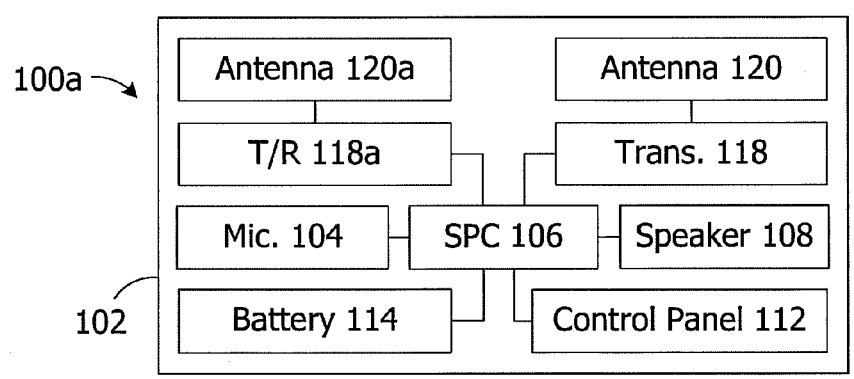
FIG. 6 is a block diagram of a hearing aid in accordance with one embodiment of a present invention.

In at least some instances, it may be desirable for the BTE hearing aid 100 to wirelessly communicate with devices other than the implanted cochlear stimulator 200. Examples of such auxiliary devices include, but are not limited to, remote controls, fitting apparatus, music players, mobile phones and contra-lateral hearing aid. Such communication may be accomplished in a variety of ways. For example, communication by way of the data transmitter 118 and antenna 120 may be time multiplexed. Alternatively, and referring to FIG. 6, the exemplary BTE hearing aid 100a is essentially identical to BTE hearing aid 100 and similar elements are represented by similar reference numerals. The BTE hearing aid 100a may be used in place of the BTE hearing aid 100 in the system in the manner described above. Here, however, an auxiliary transmitter/receiver (or "transceiver") 118a and antenna 120a create a second wireless link with an auxiliary device. For example, the wireless link created with the transmitter 118 and antenna 120 could operate at a first frequency (e.g., 13 MHz) and the transmitter/receiver 118a and antenna 120a could operate at a second frequency (e.g., 10.6 MHz) to create a pair of high bandwidth wireless links. Electrical impulses corresponding to sound are processed by the sound processor 106 for transmission to the implanted stimulator 200 in the manner described above, while control signals from a remote control or fitting apparatus are used to adjust the functionality of the BTE hearing aid 100 in conventional fashion.

There may be some instances where various factors, such as the location of the components relative to one another on the user's head, the size of the BTE hearing aid, and/or the power requirements of the BTE hearing aid, make direct data transmission from the BTE hearing aid to the implanted cochlear stimulator less than optimal. Here, a retransmission apparatus may be used to receive stimulation data from the BTE hearing aid and to transmit that stimulation data to an implanted cochlear stimulator. One example of a system that includes such a retransmission apparatus is generally represented by reference numeral 20 in FIG. 7. The elements of system 20 are essentially identical to system 10 and similar elements are represented by similar reference numerals. For example, system 20 includes a BTE hearing aid 100 (or other external hearing assistance device), an implantable cochlear simulator 200, and an external head mountable power supply 300. The BTE hearing aid 100 creates stimulation data that is supplied to the cochlear simulator 200 by way of a wireless data link, while the power supply 300 supplies power to the cochlear simulator by way of a wireless power link. Here, however, the BTE hearing aid 100 transmits the stimulation data to a retransmission apparatus 400 and the retransmission apparatus transmits the stimulation data to the cochlear simulator 200. The transmissions may occur at different frequencies such as, for example, 2.4 GHz from the BTE hearing aid 100 to the retransmission apparatus 400 and 49 MHz from the retransmission apparatus 400 to the cochlear simulator 200. The BTE hearing aid 100 may be a dual mode device that is capable of transmitting at one frequency when the retransmission apparatus 400 is employed and another frequency when it is not. Other systems may include a pair of hearing aids that transmit stimulation data at different frequencies. Here, the user will select the appropriate hearing aid depending upon the intended mode of use.

The above-described arrangement is advantageous because the retransmission apparatus 400 need not be a head mounted device and, therefore, can include a much larger battery than a BTE hearing aid and, in turn, a sensitive receiver and a powerful transmitter.

Turning to FIGS. 8 and 9, the retransmission apparatus 400 includes a housing 402, an antenna 404 that also functions as a lanyard so that the retransmission apparatus can be worn around the user's neck, and a user interface 406. A transmitter/receiver 408, controller 410 and battery 412 are located within the housing 402.

Figure 10:
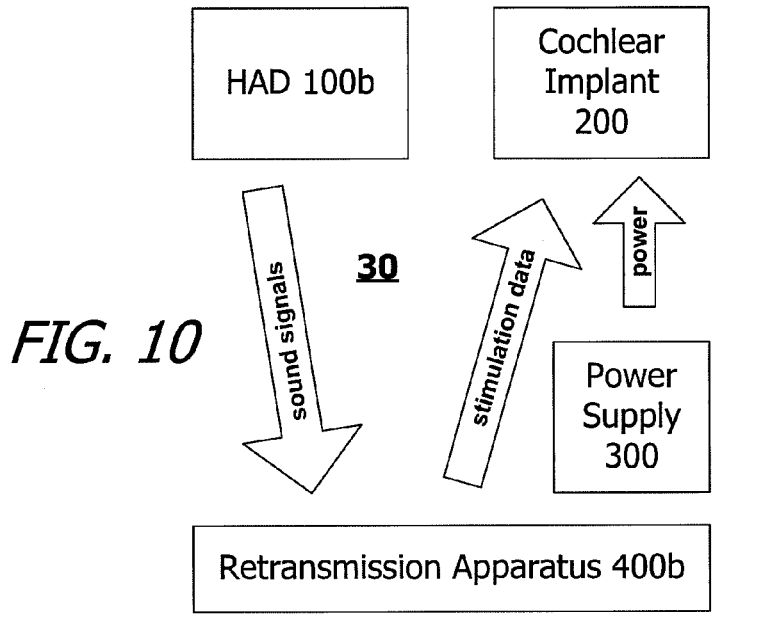
FIG. 10 is a block diagram showing components of an ICS system in accordance with one embodiment of a present invention.

Another exemplary system that employs a retransmission apparatus is generally represented by reference numeral 30 in FIG. 10. System 30 is substantially similar to system 20 and similar elements are represented by similar reference numerals. For example, the power supply 300 supplies power to the cochlear simulator 200 by way of a wireless power link. Here, however, the hearing assistance device 100b does not include sound processor circuitry. Instead of transmitting stimulation data, the hearing assistance device 100b transmits the electrical signals from a microphone to a retransmission apparatus 400b, which includes sound processor circuitry. The sound processor circuitry in the retransmission apparatus 400b converts the electrical signals from the microphone into stimulation data, and the retransmission apparatus transmits the stimulation data to the cochlear simulator 200 by way of a wireless data link.

Figure 11:
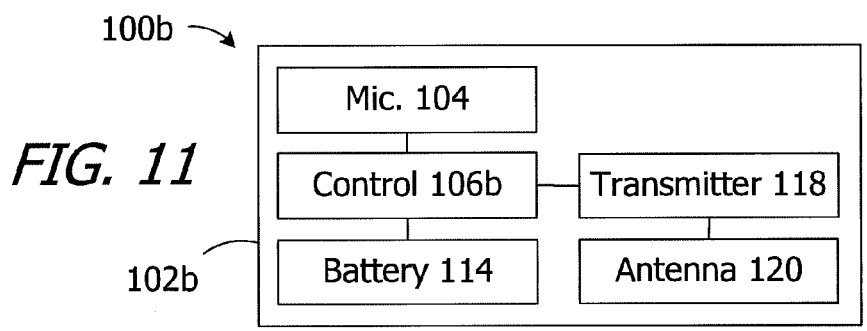
FIG. 11 is block diagram of a hearing assistance device in accordance with one embodiment of a present invention.
Figure 12:
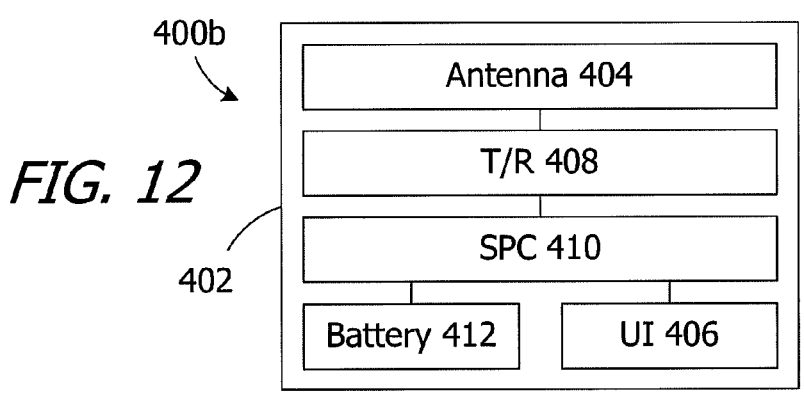
FIG. 12 is block diagram of a retransmission apparatus in accordance with one embodiment of a present invention.

Referring also to FIG. 11, the exemplary hearing assistance device 100b is a CIC device that includes a housing 102b configured to fit within the ear canal, a microphone 104, control circuitry 106b, a battery 114 and data communication apparatus (e.g., a transmitter 118 and an antenna 120) that establishes a wireless data link with the retransmission apparatus 400b. In some implementations, a speaker may be provided. BTE and ITC hearing assistance devices may also be employed. The hearing assistance device 100b does not include circuitry that generates stimulation data. Instead, the data transmitted by the communication apparatus is the electrical signals from the microphone 104. Turning to FIG. 12, the exemplary retransmission apparatus 400b includes a housing 402, an antenna 404 that also functions as a lanyard, and a user interface 406. A transmitter/receiver 408, sound processing circuitry 410 and battery 412 are located within the housing 402. The electrical signals from the microphone 104, which are received by way of the antenna 404 and transmitter/receiver 408, are processed by the sound processing circuitry 410 in the manner described above with reference to sound processing circuitry 106. The resulting stimulation data is transmitted by retransmission apparatus 400b to the cochlear simulator 200. The respective transmissions from the hearing assistance device 100b to the retransmission apparatus 400b and from the retransmission apparatus 400b to the cochlear simulator 200 may occur at different frequencies (e.g., 2.4 GHz and 49 MHz).

Figure 13:
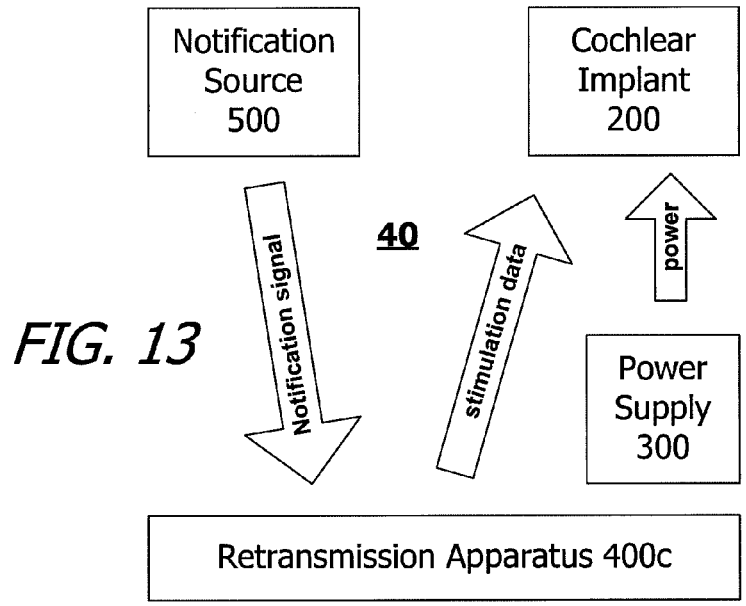
FIG. 13 is a block diagram showing components of an ICS system in accordance with one embodiment of a present invention.

Retransmission apparatus may also be used to provide stimulation data indicative of a notification when the BTE hearing aid 100 (or other external hearing assistance device) is not in use. For example, although some people may prefer to sleep without their external hearing assistance device, there are many instances where it is important that they receive audible notifications. Such audible notifications include, but are not limited to, an alarm sound (e.g., the sound from a smoke alarm, a $CO_2$ alarm, an alarm clock or home security system), telephone ringing, crying or an alarm notification from a baby monitor, and doorbell ringing. As illustrated for example in FIG. 13, the exemplary system 40 includes the aforementioned cochlear stimulator 200 and power supply 300 that supplies power to the cochlear stimulator by way of a wireless link. There is no hearing assistance device. Instead, a notification source 500 wirelessly transmits a notification signal to a retransmission apparatus 400c and the retransmission apparatus transmits stimulation data to the cochlear stimulator 200 in response. Exemplary notification sources include, but are not limited to, fire alarms, smoke alarms, $CO_2$ alarms, alarm clocks, telephones, baby monitors and doorbells. BTE and body worn sound processors, hearing aids, and other hearing assistance devices are not "notification sources." The retransmission apparatus 400c may be a bedside device that is sized for placement on a nightstand.

In those instances where the notification signal is an electronic representation of the notification (e.g., an electronic representation of the sound of a smoke alarm), the retransmission apparatus 400c converts the notification signal into stimulation data and transmits the stimulation data to the cochlear stimulator 200 in a manner similar to retransmission device 400b. In other implementations, the notification signal may simply be a predefined trigger signal or one of a plurality of different trigger signals. Here, the retransmission apparatus 400c will transmit predefined stimulation data to the cochlear stimulator 200 (e.g., data that corresponds to a predefined sound or series of sounds) in response to the trigger signal. In still other implementations, the notification signal may be the actual audible notification from the notification source. Here, the retransmission apparatus 400c will include a microphone that converts the audible notifications into electrical signals and a controller that determines whether the electrical signals correspond to an alarm or other predetermined notification as opposed to background noise, speech, and other non-notification sounds. If so, the electrical signals are converted into stimulation data by the retransmission apparatus 400c and the stimulation data is transmitted to the cochlear stimulator 200. In any case, the resulting stimulation of the cochlea should be sufficient to wake a sleeping person.

Figure 14:
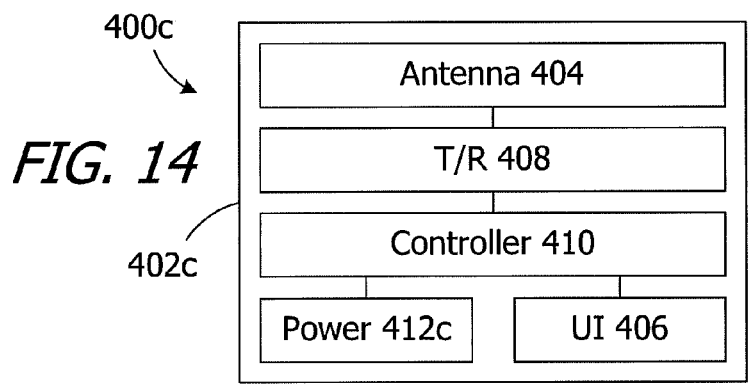
FIG. 14 is block diagram of a retransmission apparatus in accordance with one embodiment of a present invention.

Referring to FIG. 14, the exemplary retransmission apparatus 400c includes a housing 402c, an antenna 404, and a user interface 406. A transmitter/receiver 408, a controller 410, and a power supply 412c are located within the housing 402c. The wirelessly transmitted notification signals from the notification source 500 (e.g., a wirelessly transmitted data signal) are received by way of the antenna 404 and transmitter/receiver 408, and are processed by the controller 410. The resulting stimulation data is transmitted by the retransmission apparatus 400c to the cochlear simulator 200 by way of the antenna 404 and transmitter/receiver 408. The transmissions may occur at different frequencies such as, for example, 2.4 GHz Bluetooth transmission from the notification source 500 to the retransmission apparatus 400c, and 49 MHz transmission from the retransmission apparatus 400c to the cochlear simulator 200. In other implementations, a separate antenna and transmitter/receiver may be provided for the notification source to retransmission apparatus wireless link and for the retransmission to cochlear stimulator wireless link.

Figure 15:
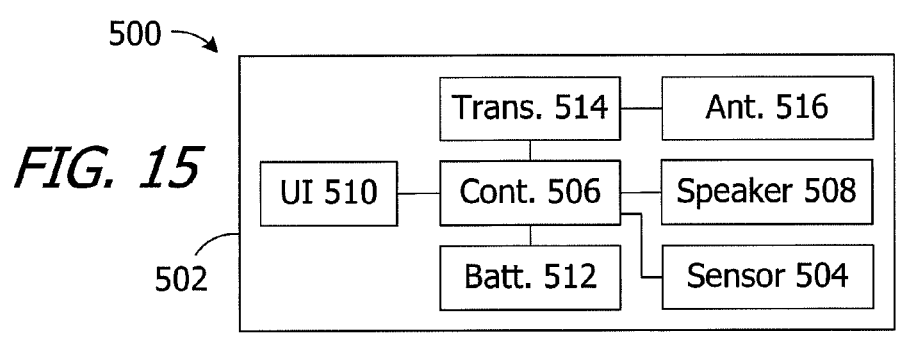
FIG. 15 is a block diagram of a notification source in accordance with one embodiment of a present invention.

Turning to FIG. 15, and although the present notification sources are not so limited, the exemplary notification source 500 is in the form of a smoke alarm that includes conventional smoke alarm components such as a housing 502, a smoke sensor 504, a controller 506, a speaker or other sound generator 508, a user interface 510 and a battery 512. The exemplary notification source 500 also includes a transmitter 514 and antenna 516. In response to a signal from the sensor 504, the controller 506 causes sound to be emitted from the speaker 508. The controller 506 also causes the notification signal to be transmitted to the retransmission apparatus 400c by way of the transmitter 514 and antenna 516.

It should also be noted that the notification source and the retransmission apparatus may be combined in some instances.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. The inventions also include systems that include an external hearing assistance device in the form of a BTE cochlear implant sound processor that is modified to include the wireless data transmission capability described above. It is intended that the scope of the present inventions extend to all such modifications and/or additions and that the scope of the present inventions is limited solely by the claims set forth below.

We claim:

1. A hearing assistance system, comprising:
   an implantable cochlear stimulator including a position element, a power receiver apparatus, an electrode array, a stimulation data receiver apparatus, and a stimulation processor operably connected to the stimulation data receiver apparatus and to the electrode array, and not including a battery;
   an external hearing assistance device including an external hearing device housing, a battery, sound processor circuitry located within the external hearing device housing that converts electrical signals from a microphone into stimulation data, and a data communication apparatus configured to wirelessly transmit the stimulation data; and
   a head mountable power supply including a head mountable power supply housing, a battery located within the head mountable power supply housing, a magnet that is magnetically attracted to the position element, and a power transmission apparatus operably connected to the battery and configured to wirelessly supply power to the implantable cochlear stimulator power receiver apparatus.

2. A hearing assistance system as claimed in claim 1, wherein the implantable cochlear stimulator does not include sound processor circuitry.

3. A hearing assistance system as claimed in claim 1, wherein the external hearing assistance device includes a speaker.

4. A hearing assistance system as claimed in claim 1, wherein the external hearing assistance device is not connected to the head mountable power supply by a cable.

5. A hearing assistance system as claimed in claim 1, wherein the external hearing assistance device comprises a BTE hearing assistance device.

6. A hearing assistance system as claimed in claim 1, wherein the data communication apparatus of the external hearing assistance device comprises a transmitter and an antenna.

7. A hearing assistance system as claimed in claim 1, wherein the stimulation data receiver apparatus of the implantable cochlear stimulator wirelessly receives stimulation data directly from the data communication apparatus of the external hearing assistance device.

8. A hearing assistance system as claimed in claim 1, wherein the head mountable power supply does not include sound processor circuitry.

9. A hearing assistance system as claimed in claim 1, wherein the head mountable power supply does not generate, receive or transmit stimulation data.

10. A hearing assistance system as claimed in claim 1, further comprising:
a retransmission apparatus that wirelessly receives stimulation data from the external hearing assistance device and transmits the received stimulation data to the implantable cochlear stimulator.

11. A hearing assistance method, comprising the steps of:
wirelessly transmitting stimulation data from an external hearing assistance device associated with a user's head to a cochlear stimulator that does not include a battery that is implanted within the user's head;
wirelessly transmitting power stored in a battery of an external power supply, which is not connected to hearing assistance device and is mounted on the exterior of the user's head in spaced relation to the external hearing device by way of magnetic attraction between the power supply and the implanted cochlear stimulator, to the implanted cochlear stimulator; and
electrically stimulating the user's auditory nerves with the implanted cochlear stimulator in response to receipt of the stimulation data from the external sound processor.

12. A hearing assistance method as claimed in claim 11, further comprising the step of:
converting electrical signals from a microphone into the stimulation data with a sound processor located within the external hearing assistance device.

13. A hearing assistance method as claimed in claim 11, further comprising the step of:
powering the implanted cochlear stimulator solely with power wirelessly received from the battery of the external power supply mounted on the exterior of the user's head.

14. A hearing assistance method as claimed in claim 11, wherein the step of wirelessly transmitting power comprises wirelessly transmitting power from the external power supply to the implanted cochlear stimulator with an inductive link that does not include data.

15. A hearing assistance method as claimed in claim 11, wherein the step of wirelessly transmitting power comprises wirelessly transmitting power from the external power supply that does not include sound processing functionality.

16. A hearing assistance method as claimed in claim 11, wherein the step of wirelessly transmitting stimulation data comprises wirelessly transmitting stimulation data to a retransmission device that is worn by the user and wirelessly transmitting the stimulation data from the retransmission device to the implanted cochlear stimulator.

17. A hearing assistance system, comprising:
an implantable cochlear stimulator including a position element, a power receiver apparatus, an electrode array, a stimulation data receiver apparatus, and a stimulation processor operably connected to the stimulation data receiver apparatus and to the electrode array and not including a battery;
a hearing assistance device, including a battery, a microphone that converts sound pressure waves into electrical signals, and data communication apparatus that wirelessly transmits the electrical signals;
a retransmission apparatus, including a data communication apparatus and sound processor circuitry, that wirelessly receives electrical signals from the hearing assistance device, converts the electrical signals from a microphone into stimulation data, and wirelessly transmits the stimulation data to the implantable cochlear stimulator; and
a head mountable power supply including a battery, a magnet that is magnetically attracted to the position element, and a power transmission apparatus operably connected to the battery and configured to wirelessly supply power to the implantable cochlear stimulator power receiver apparatus.

18. A hearing assistance system as claimed in claim 17, wherein the implantable cochlear stimulator does not include sound processor circuitry.

19. A hearing assistance system as claimed in claim 17, wherein the hearing assistance device is not connected to the head mountable power supply by a cable.

20. A hearing assistance system as claimed in claim 17, wherein the hearing assistance device comprises a CIC hearing assistance device.

21. A hearing assistance system as claimed in claim 17, wherein the data communication apparatus of the hearing assistance device comprises a transmitter and an antenna.

22. A hearing assistance system as claimed in claim 17, wherein the head mountable power supply does not include sound processor circuitry.

23. A hearing assistance system as claimed in claim 17, wherein the head mountable power supply does not generate, receive or transmit stimulation data.

24. A hearing assistance system, comprising:
an implantable cochlear stimulator including a position element, a power receiver apparatus, an electrode array, a stimulation data receiver apparatus, and a stimulation processor operably connected to the stimulation data receiver apparatus and to the electrode array, and not including a battery;
a notification source that transmits a notification signal;
a retransmission apparatus, including a data communication apparatus, that wirelessly receives the notification signal and wirelessly transmits stimulation data to the implantable cochlear stimulator in response to receipt of the notification signal; and
a head mountable power supply including a battery, a magnet that is magnetically attracted to the position element, and a power transmission apparatus operably connected to the battery and configured to wirelessly supply power to the implantable cochlear stimulator power receiver apparatus.

25. A hearing assistance system as claimed in claim 24, wherein the notification signal comprises one or more of an electronic representation of a notification sound, a trigger signal, and an audible notification.

26. A hearing assistance system as claimed in claim 24, wherein the head mountable power supply does not include sound processor circuitry.

27. A hearing assistance system as claimed in claim 24, wherein the head mountable power supply does not generate, receive or transmit stimulation data.

* * * * *